United States Patent [19]

Landis

[11] Patent Number: 4,852,186

[45] Date of Patent: Aug. 1, 1989

[54] COMBINED VISOR AND PROTECTIVE SHIELD

[76] Inventor: Timothy J. Landis, 2006 McLaren Dr., Roseville, Calif. 95661-4945

[21] Appl. No.: 229,349

[22] Filed: Aug. 8, 1988

Related U.S. Application Data

[63] Continuation-in-part of Ser. No. 194,150, May 16, 1988.

[51] Int. Cl.$^4$ ............................ A61F 9/00; A42B 1/06
[52] U.S. Cl. .................................................. 2/9; 2/10; 2/196
[58] Field of Search ............ 2/9, 10, 11, 12, DIG. 11

[56] References Cited

U.S. PATENT DOCUMENTS

| | | | |
|---|---|---|---|
| D. 228,700 | 10/1973 | Gager | 2/10 X |
| 2,179,719 | 11/1939 | Goskey | 2/10 |
| 2,638,593 | 5/1953 | Eloranta | 2/12 |
| 3,049,716 | 8/1962 | Stegeman | 2/12 X |
| 3,555,562 | 1/1971 | Patton, Jr. | 2/10 |
| 4,317,238 | 3/1982 | Amen | 2/DIG. 11 X |
| 4,701,965 | 10/1987 | Landis | 2/9 X |

Primary Examiner—Werner H. Schroeder
Assistant Examiner—Jeanette E. Chapman
Attorney, Agent, or Firm—Julian Caplan

[57] ABSTRACT

To protect dentists, physicians, their assistants and others from contamination from contact with blood, bodily fluids and the like of patients, a transparent shield extends from the forehead to below the mouth and partially around the sides of the face. The shield is supported spaced from the face by a visor extending forward from the forehead. The visor is supported by a band around the back of the head. The present invention fabricates the shield, visor and head bands from a single blank, suitably die cut, all interconnected. The combined shield, visor and head bands may be attached to a surgeon's cap or the head bands may be eliminated and the cap attached to the inner edge of the visor.

12 Claims, 2 Drawing Sheets

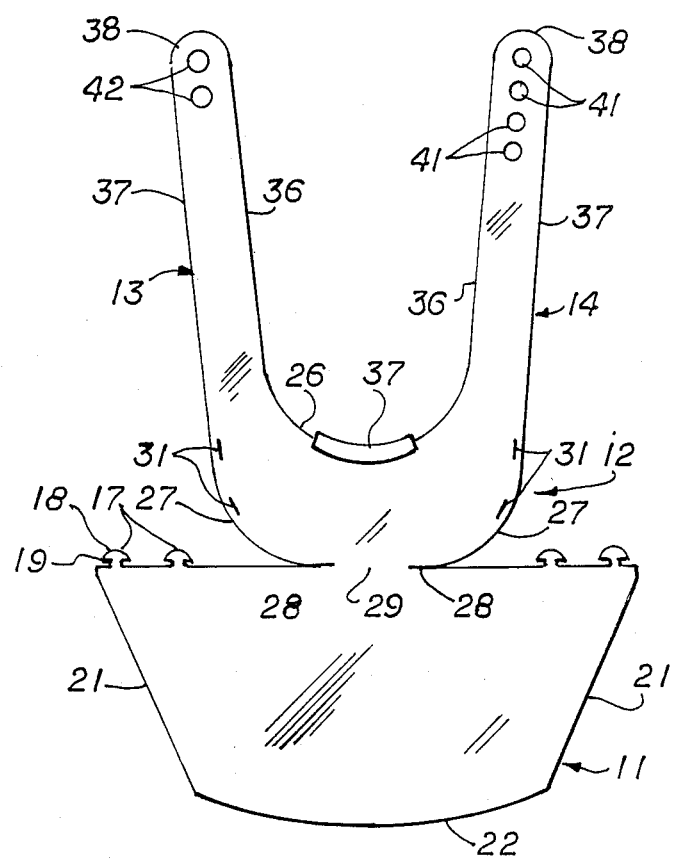
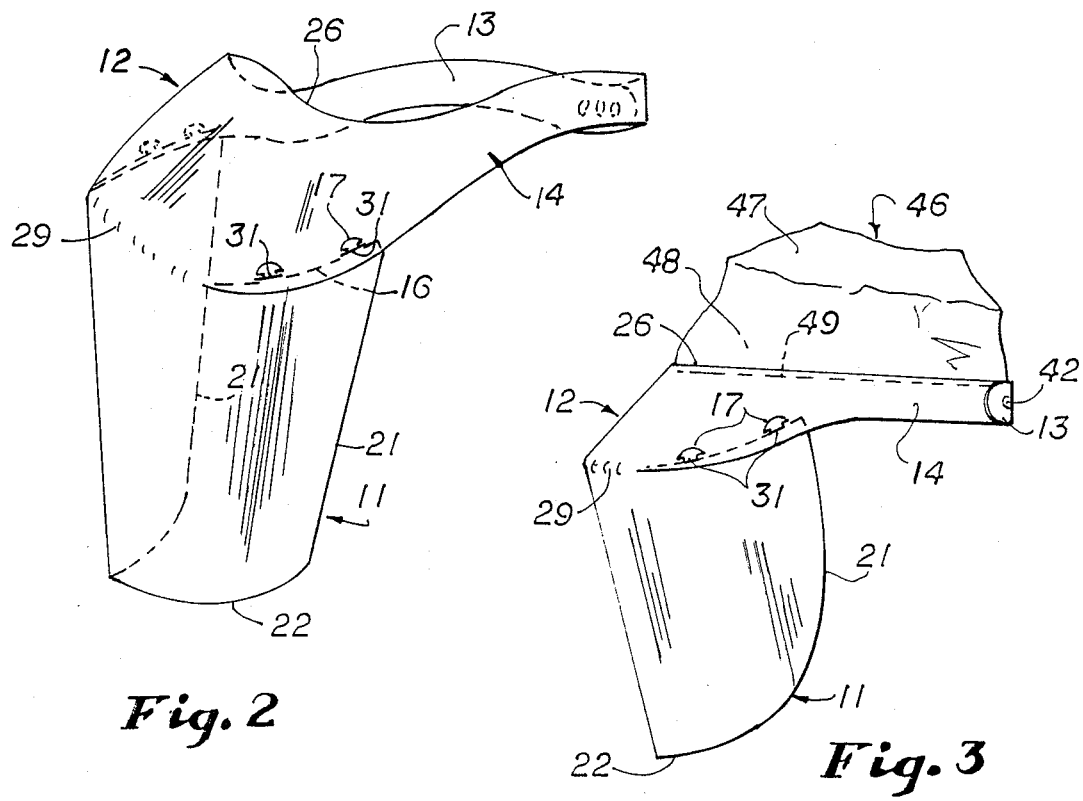

COMBINED VISOR AND PROTECTIVE SHIELD

CROSS-REFERENCE TO RELATED APPLICATIONS

This application is a continuation-in-part of my copending application Ser. No. 07/194,150 filed May 16, 1988 on PROTECTIVE SHIELD AND VISOR SUPPORTING SAME. The application is also an improvement upon my U.S. Pat. No. 4,701,965.

BACKGROUND OF THE INVENTION

1. Field of the Invention

This invention relates to a new and improved mask for use by surgeons, dentists and others to avoid contamination with germs and viruses of their patients and customers. A visor, which is adjustable to fit the head size of the wearer, supports a transparent plastic shield of sheet plastic which is integral with the visor but is bent with respect thereto. The shield extends down to below the level of the mouth of the wearer and around the sides of the face, thus providing superior, frontal and lateral protection from splashing and spattering with bodily fluids.

2. Related Art Surgical masks of gauze and paper have been used to prevent intercontamination of doctor and patient.

However, wearing such masks is hot and uncomfortable and, frequently, frightening to patients. Putting the masks on and removing them are time-consuming and sometimes difficult. Breath condenses within the mask and hence the latter becomes saturated with moisture and thereby fails to be an effective barrier to viruses and bacteria.

Surgical masks cause the wearer to re-inhale exhaled breath causing the $CO_2$ content of the blood to rise. The result of this may be increased heart and respiration rates and higher body temperatures, perspiration, fogged glasses and goggles.

U.S. Pat. No. 4,701,965 illustrates a visor-type mask for dentists and dental technicians which is commercially successful. This reference shows a visor which attaches to the head and a transparent shield supported thereby. The present invention differs from said patent in that the visor and shield and, optionally, the bands which attach behind the head of the wearer are formed of a single blank and are thus permanently connected together. The construction has very important fabrication and assembly advantages.

SUMMARY OF THE INVENTION

A thin sheet of transparent plastic is formed in a flat blank. The shield portion of the device has a substantially straight top edge, converging sides and a bottom. Projecting upward from the top edge are spaced tabs. Connected to and integral with the shield is a visor portion which has inner and outer curved edges, the center of the outer curved edge being joined to the top edge of the shield at a hinge line. Slits are spaced along the outer edge of the visor to receive the tabs. Bands extend rearward of the visor and the outer ends thereof have cooperating fastening means such as snaps, buckles, adhesive strips, Velcro-like materials and other suitable devices. Alternatively, elastic bands or stretchable tubing may be attached to the rear ends of the bands. A protective pad is preferably glued to the inner edge of the visor to prevent the latter from cutting the forehead of the wearer. To assemble the device, the shield is bent at the hinge line approximately 90° with respect to the visor. Obviously, this step is preferably done at the place of manufacture although it may be done by the consumer. The tabs on the upper edge of the shield are inserted through the slits in the visor. Thereby the shield is bent in arcuate form when viewed in cross-section. The bands on the ends of the visor are brought around the back of the head and fastened together. Alternatively a surgeon's cap may be attached to the inner edge of the visor and to the inner edges of the bands so that as a single unit a head protecting surgeon's cap, a visor and a shield are donned by the wearer all at one time.

BRIEF DESCRIPTION OF THE DRAWINGS

Figure 4:
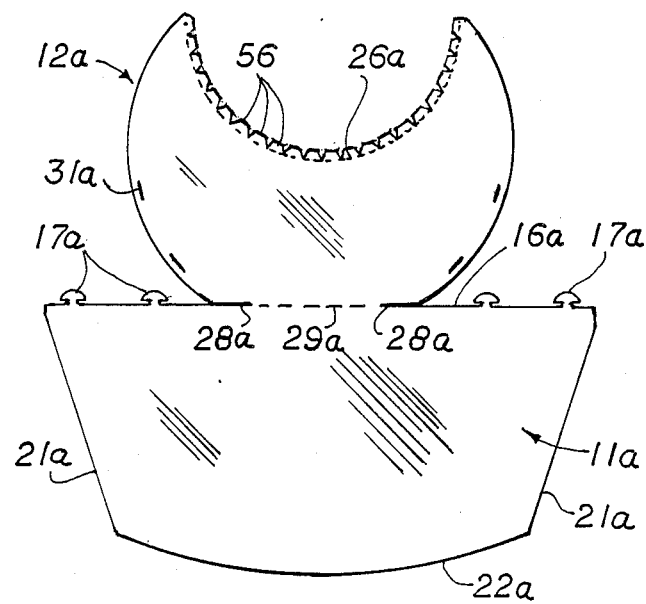

IN THE DRAWINGS:

FIG. 1 is a blank for the device;

FIG. 2 is a perspective view of the device assembled;

FIG. 3 is a view similar to FIG. 2 showing the device with a surgeon's cap attached;

FIG. 4 is a view similar to FIG. 1 of a modification; and

Figure 5:
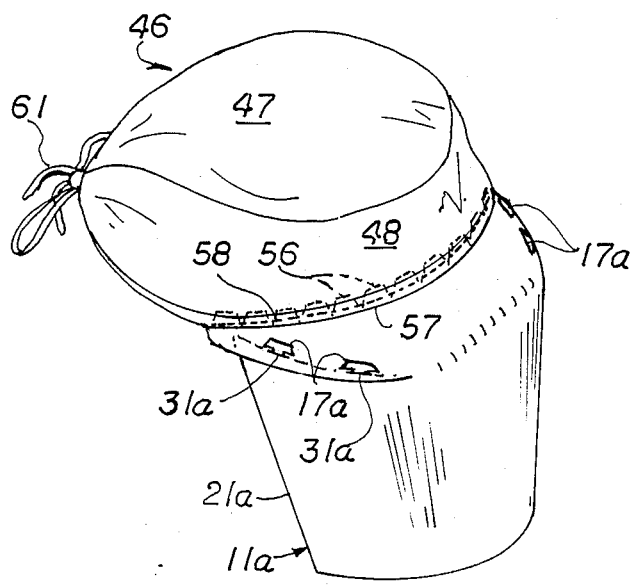

FIG. 5 is a view similar to FIG. 3 showing the modification of FIG. 4 attached to a surgeon's cap.

Figure 6:
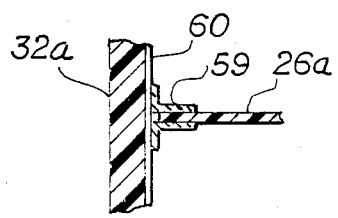

FIG. 6 is an enlarged, fragmentary view of another modification.

DESCRIPTION OF PREFERRED EMBODIMENTS

The blank shown in FIG. 1 consists of a shield portion 11, a visor or spacer portion 12, a first headband 13 and a second headband 14 said head bands comprising first and second attachment means.

Considering now shield 11, the latter has a top horizontal edge 16 from which project upwardly spaced tabs 17 (here shown as 4 in number). Each tab has a curved upper edge 18 and notches 19 cut therein at the level of the top edge 16. Shield 11 has downward converging sides edges 21 and a bottom edge 22.

Visor 12 is integral with shield 11. It has an inner edge 26 shaped to fit around the forehead of the wearer and side outer edge portions which are arcuate, having a radius of curvature greater than that of inner edge 26. Horizontal cuts 28 are formed at the juncture of visor 12 and shield 11 extending inward toward the center leaving an imperforate hinge area 29. Spaced slits 31 are formed in visor 12 spaced inward from outer edge portions 27 to mate with the tabs 17. Many other ways to secure edge 16 to visor 12 such as hooks, snaps, gluing, adhesive tape, Velcro-type materials, snaps, clips, solvent bonding, ultra-sonic welding, laser fusion, and others (not shown) will readily occur to those skilled in this art. To prevent the edge 26 from cutting into the forehead of the wearer, a foam rubber or foam plastic pad 32 may be glued or otherwise attached to the middle of edge 26.

As shown in FIG. 6, a pad 32a has a clip 59 which snaps onto the inner edge 26a. The pad 32a is preferably attached to a flat member 60 (to secure better adhesion) and clip 59 is attached to the other surface thereof.

In the form of the invention shown in FIG. 1, each band 13, 14 has an inner edge 36 which is a rearward extension of edge 26 and an outer edge 37 which is a continuation of edge portions 27, the edges 36 and 37 preferably being substantially parallel. Ends 38 are preferably curved. As shown in FIG. 1, there are two male stud fasteners 42 attached near the outer edge of bands 13 and a series of spaced holes 41 near the outer edge of band 14. The fasteners 42 may be inserted through the holes 41 in such manner as to accommodate the head size of the wearer. As has been mentioned, many other means may be used to attach the bands 13 and 14 together such as buckles, hooks, adhesives, Velcro-like materials and the like (not shown). Alternatively, the bands 13, 14 may be made shorter than shown in FIG. 1 and an elastic band or tape or stretchable tubing may be used to interconnect the ends of bands 13 and 14, the attachment means stretching to accommodate the head size of the wearer. Attachment of the device to the head of the wearer may be by other means.

In assembling the device, visor portion 12 is bent approximately at right angles to the shield portion 11 along the hinge area 29. Thereupon the tabs 17 are inserted through the appropriate slits 31 thereby bending the shield 11 in arcuate form so that it covers the sides of the face of the wearer. The device may be shipped from the factory flat or bent at hinge area 29 or with the shield curved by reason of the tabs 17 being inserted in the slits 31, at the option of the maker. The consumer completes the assembly of the device if this has not been done at the factory and then passes the bands 13, 14 around the back of the head, fastening the ends of the bands in whatever manner is desired.

A modification of the structure of FIG. 2 is shown in FIG. 3. A surgeon's cap 46 of the type commonly used to cover the head of operating room personnel has a crown 47 and sides 48, preferably formed of paper or non-woven fiber. Various attachment means such as the seam 49 shown in FIG. 3 attach the lower edges of the sides 48 to the visor 12 and bands 13.

Directing attention now to FIGS. 4 and 5, the means of attachment of the device to the head of the wearer is a surgeon's cap which is in turn attached to the inner edge of the visor. There are many different styles of surgeon's cap presently on the market and the present invention is believed to be suitable for use with any of them. The combination shield and visor 11a, 12a shown in FIG. 4 resembles that of FIG. 1 except that a plurality of trapezoidal tabs 56 are formed on the inner edge 26a of the visor 12a. Such tabs 56a are bent upward and are sewn, stapled or otherwise attached to the lower edge of the sides 48a of the cap 46a. In one common type of surgeon's cap, a reinforcement 47 consisting of a narrow reinforcement tape is folded around the lower edge of the sides 48 and sewn thereto by stitching 58. This same stitching 58 may be used to attach the tabs 56 to the sides 48a. In the type surgeon's cap shown in FIG. 5, the reinforcement 57 is continued rearwardly forming ties 61 which are tied in a knot behind the head of the wearer to accommodate different head sizes.

The form of the invention shown in FIGS. 4 and 5 resembles that of the preceding modification and corresponding reference numerals followed by the subscript a are used to designate corresponding parts. A principal difference between the two modifications is the fact that there are no headbands such as those designated reference numerals 13 and 14 in FIGS. 1-3.

What is claimed is:

1. A protective device comprising a unitary blank of thin, transparent material comprising a shield portion, a spacer portion and means to attach said blank portion to the head of a wearer,
   said shield portion having a top edge, sides and a bottom and first attachment means located near said top edge,
   said spacer portion having a curved inner edge to conform to the shape of the forehead of the wearer and a curved outer edge, a hinge section comprising a portion of said outer edge and a portion of said top edge shield, and second attachment means located near said outer edge,
   said first and second attachment means being cooperable to be engaged to cause the top edge of said shield to conform substantially to the shape of said outer edge.

2. A device according to claim 1 in which said first and second attachment means comprises interfitting tabs and slits.

3. A device according to claim 1 in which said first attachment means comprises spaced tabs extending up from said top edge and said second attachment comprises correspondingly spaced slits formed in said spacer portion spaced inward of said outer edge.

4. A device according to claim 3 in which said top edge is substantially straight and said blank is formed with cuts extending inward and constituting extending of said top edge, the inner ends of said cuts being spaced apart by said hinge section.

5. A device according to claim 1 which further comprises a protective pad on said inner edge and means securing said pad to said spacer portion.

6. A device according to claim 1 in which said means to attach said blank portion comprises an integral extension of said spacer portion on either side of said spacer portion and cooperable fastening means on the ends of said extension.

7. A device according to claim 6 in which said extensions are thin straps extending substantially perpendicular to said top edge.

8. A device according to claim 1 which further comprises a surgeon's cap having lower edges, said lower edges being attached to the middle of said inner edge and partially to said means to attach said spacer portion to the head.

9. A device according to claim 8 in which said inner edge is formed with tabs and which further comprises means to attach said tabs to said lower edges.

10. A device according to claim 8 which further comprises a reinforcement tape fixed to said lower edges, said reinforcement tape extending beyond said lower edges to form ties adapted to be knotted behind the head of the wearer to hold said device on the head.

11. A device according to claim 10 which further comprises stitching attaching said reinforcement tape to said lower edges.

12. A device according to claim 11 in which said inner edge of said spacer is formed with tabs, said stitching attaching said tabs to said cap.

* * * * *